United States Patent
Sun et al.

(10) Patent No.: US 10,350,045 B2
(45) Date of Patent: Jul. 16, 2019

(54) REPAIR MATERIAL WITH MULTI-PURPOSE FOR ABDOMINAL WALL HERNIA

(71) Applicant: TransEasy Medical Tech.Co.,Ltd, Beijing (CN)

(72) Inventors: Jie Sun, Beijing (CN); Fan Chen, Beijing (CN); Hongying Qiao, Beijing (CN); Lingcui Ding, Beijing (CN); Kai Meng, Beijing (CN)

(73) Assignee: TransEasy Medical Tech.Co., Ltd, Beijing (CN)

( * ) Notice: Subject to any disclaimer, the term of this patent is extended or adjusted under 35 U.S.C. 154(b) by 526 days.

(21) Appl. No.: 15/142,922

(22) Filed: Apr. 29, 2016

(65) Prior Publication Data

US 2016/0242891 A1 Aug. 25, 2016

(30) Foreign Application Priority Data

| Jan. 25, 2016 | (CN) | .......................... 2016 1 0051690 |
| Jan. 25, 2016 | (CN) | .......................... 2016 1 0051761 |
| Jan. 25, 2016 | (CN) | .......................... 2016 1 0051762 |
| Jan. 25, 2016 | (CN) | .......................... 2016 1 0051763 |
| Jan. 25, 2016 | (CN) | ..................... 2016 2 0073761 U |

(51) Int. Cl.
| *A61L 2/00* | (2006.01) |
| *A61F 2/00* | (2006.01) |
| *A61L 31/04* | (2006.01) |
| *A61L 31/10* | (2006.01) |
| *A61L 31/14* | (2006.01) |

(52) U.S. Cl.
CPC .......... *A61F 2/0063* (2013.01); *A61L 31/048* (2013.01); *A61L 31/10* (2013.01); *A61L 31/148* (2013.01); *A61F 2210/0004* (2013.01)

(58) Field of Classification Search
CPC .......... A61F 2/0063; A61F 2210/0004; A61L 31/048; A61L 31/10; A61L 31/148
See application file for complete search history.

(56) References Cited

U.S. PATENT DOCUMENTS

2004/0146546 A1* 7/2004 Gravett .................... A61F 2/06
424/445

* cited by examiner

*Primary Examiner* — Cephia D Toomer

(57) ABSTRACT

A repair material with multi-purpose for an abdominal wall hernia of the present invention relates to a technical field of medical consumables, which includes technical field of medical consumables. In the MPEG-PLLA copolymer, a molecular weight of MPEG is 2000-10000, and a molecular weight of PLLA is 3000-8000. Compared with PLCL, the repair material of the present invention is significantly improved in water absorption of the absorbable membrane to ameliorate healing effects, and a contact angle is greatly reduced. As a result, postoperative abdominal wall compliance is sufficient, which basically provides no discomfort. Therefore, compared with the PLCL, the present invention is more comfortable. In addition, the repair material of the present invention doesn't need to be heat-fitted, and polypropylene is completely fitted with the absorbable membrane, wherein no obvious boundary face is observed through a microscope, and separation never occurred.

8 Claims, 5 Drawing Sheets

REPAIR MATERIAL WITH MULTI-PURPOSE FOR ABDOMINAL WALL HERNIA

CROSS REFERENCE OF RELATED APPLICATION

The present invention claims priority under 35 U.S.C. 119(a-d) to CN 201610051762.3, filed Jan. 25, 2016; CN 201610051761.9, filed Jan. 25, 2016; CN 201610051763.8, filed Jan. 25, 2016; CN 201610051690.2, filed Jan. 25, 2016; and CN 201620073761.4, filed Jan. 25, 2016.

BACKGROUND OF THE PRESENT INVENTION

Field of Invention

The present invention relates to a technical field of medical consumables, and more particularly to a repair material with multi-purpose for an abdominal wall hernia.

Description of Related Arts

Hernia is a fascial defect in structure. For example, an organ or part of the organ, or a tissue or part of the tissue is able to be extended through the fascial defect of an abdominal wall. Commonly, the hernia structurally comprises weakened, bulged or actually torn fascia of an organ or a tissue. There are many types of hernias. For example, if happening to a lower abdominal area, the hernia often contains intra-abdominal contents such as intestines or other tissues which enter or pass through the abdominal wall defect. Mesh patch is widely used in hernia repair. Conventionally, widely used patches are polyester meshes (such as Dacron and Mersilene), and polypropylene meshes (such as Marlex, Prolene, etc.). However, a simple non-degradable mesh is not suitable for intra-peritoneal implantation, because organ adhesions may occur with the patch, leading to serious complications such as infertility, chronic pelvic pain, intestinal fistula, intestinal obstruction, etc. A common solution is inserting a physical barrier at a position where adhesions are undesirable. However, this barrier leads to connecting problems in the interior of the barrier, because if the barrier is prepared by a non-absorbable material, the barrier itself becomes an adhesion source; if the barrier is absorbable, absorption must be non-inflammatory, for not leading to self-adhesion.

The ePTFE developed by Gore Company is an adhesion layer resistance product (Gore-Tex® Surgical Membrane), which provides effective tissue separation. However, the material is easy to cause infection, and must be removed through a second surgery after infection. In addition, due to a high material shrinkage rate, mesothelial cells are not able to grow into the material, so it is difficult to form a new peritoneum (Harrell A G, Novitsky Y W, Peindl R D, et al. Prospective evaluation of adhesion formation and shrinkage of intra-abdominal prosthetics in a rabbit model Am Surg 2006, 72: 808-14.).

International patent WO2009079271A2 discloses a Proceed multi-layer mesh developed by American Johnson & Johnson Company, wherein the multi-layer mesh comprises a polypropylene mesh layer, a poly-dioxanone layer (PDS) and an oxidized regenerated cellulose membrane layer (ORC). A composite method thereof comprises directly thermal-pressing an ORC knitted mesh having a certain moisture content with a PDS membrane and a polypropylene mesh, and increasing binding forces between different layers with the moisture content. However, a sample prepared by the method is easy to be separated, wherein the layers of the sample are able to be separated by a tensile testing machine, and softness thereof is poor, which means a compliance with the abdominal wall needs to be improved. As a result, there will be a strong foreign body sensation after implantation.

U.S. Pat. No. 6,451,032B1 discloses a Parietex mesh of Tyco Company, comprising a mesh woven by polyethylene terephthalate yarn, composite collagen, polyethylene glycol and glycerin; wherein a collagen solution is oxidized by periodic acid for self-crosslinking, and forms a first layer with the polyethylene glycol and the glycerol; a second layer is basically the same as the first layer. The first layer and the second layer are composited with the polyethylene terephthalate mesh for achieving multi-layer composite. According to the method, chemical reactions are involved and strong oxidizing agents are used. Furthermore, direct binding between the mesh and natural macromolecule collagen which is difficult to form a membrane is not stable.

Chinese patent CN101035574A and international patent WO 2005105172A1 both disclose a Sepramesh mesh developed by BARD Company, which is a double-layer mesh woven by polypropylene yarn and polyglycolic acid yarn. The double-layer is formed by immersing a polyglycolic acid layer in a modified hyaluronic acid/carboxymethyl cellulose solution and a modified polyethylene glycol solution, wherein the hyaluronic acid/carboxymethyl cellulose is crosslinked by a carbodiimide type crosslinking agent; a polyethylene glycol derivative is acrylate-terminated; and polymerization in the solution is initiated by light. Preparation of the product involves a lot of chemical reactions, which is complex and greatly increases manufacturing costs during production.

The above mentioned products have problems such as complicated preparation processes, a lot of chemical reactions, layers which are easy to be separated, poor softness and controversial anti-adhesion effects, and prices of the above products are very high.

SUMMARY OF THE PRESENT INVENTION

For overcoming the above technical problems in the conventional technologies, an object of the present invention is to provide a repair material with multi-purpose for an abdominal wall hernia.

Accordingly, the repair material with multi-purpose for an abdominal wall hernia comprises an absorbable membrane, wherein the absorbable membrane is prepared with a mixed solution of a PLCL and an MPEG-PLLA copolymer.

The PLCL is an L-lactide/caprolactone copolymer, wherein in the L-lactide/caprolactone copolymer, a mole ratio between L-lactide and caprolactone is 50:50-90:10; and an intrinsic viscosity of the L-lactide/caprolactone copolymer at 25° C. is 1.0-2.5 dl/g.

The MPEG-PLLA copolymer, a molecular weight of MPEG is 2000-10000, and a molecular weight of PLLA is 3000-8000. Preferably, the molecular weight of the MPEG is 2000-5000, and the molecular weight of the PLLA is 5000-6000.

A mole ratio between the PLCL and the MPEG-PLLA copolymer in the mixed solution is 5:5-7:3.

The repair material comprises a polypropylene mesh with an absorbable coating thereon, and the absorbable membrane press-fitted on the polypropylene mesh; the absorbable coating is formed by applying the mixed solution of the PLCL and the MPEG-PLLA copolymer to the polypropylene mesh.

A density of the polypropylene mesh is 20-80 g/m$^2$, and a thickness thereof is 1-5 mm. Preferably, the density of the polypropylene mesh is 20-50 g/m², the thickness thereof is 1-3 mm; and a single hole area of the polypropylene mesh is 3-20 mm².

The absorbable membrane has a drainage hole thereon.

The present invention also provides a method for preparing a repair material with multi-purpose for an abdominal wall hernia.

The method comprises steps of:

(1) immersing a polypropylene mesh into a mixed solution for forming an absorbable coating on a surface of the polypropylene mesh after being dried;

(2) pouring the mixed solution into a mould, statically evaporating for obtaining an absorbable membrane; and (3) press-fitting the polypropylene mesh obtained in the step (1) to the absorbable membrane and statically evaporating;

wherein the mixed solution is a mixed solution of a PLCL and an MPEG-PLLA copolymer.

The repair material of the present invention is suitable for abdominal wall defects due to incisional hernia, parastomal hernia, umbilical hernia, inguinal hernia and peritoneal tumor resection, and is applicable to intra-abdominal hernia repair of abdominal wall hernia and the abdominal wall defects, as well as laparoscopic inguinal hernia. Compared with the prior art, the present invention has beneficial effects as follows.

Compared with the PLCL, the repair material of the present invention is significantly improved in water absorption of the absorbable membrane. A material rigidity is lowered to ameliorate healing effects, and a contact angle is greatly reduced. As a result, postoperative abdominal wall compliance is sufficient, which basically provides no discomfort. Therefore, compared with the PLCL, the present invention is more comfortable. In addition, in the repair material of the present invention, polypropylene is completely fitted with the absorbable membrane, wherein no obvious boundary face is observed through a microscope, and separation never occurred.

These and other objectives, features, and advantages of the present invention will become apparent from the following detailed description, the accompanying drawings, and the appended claims.

Figure 1:
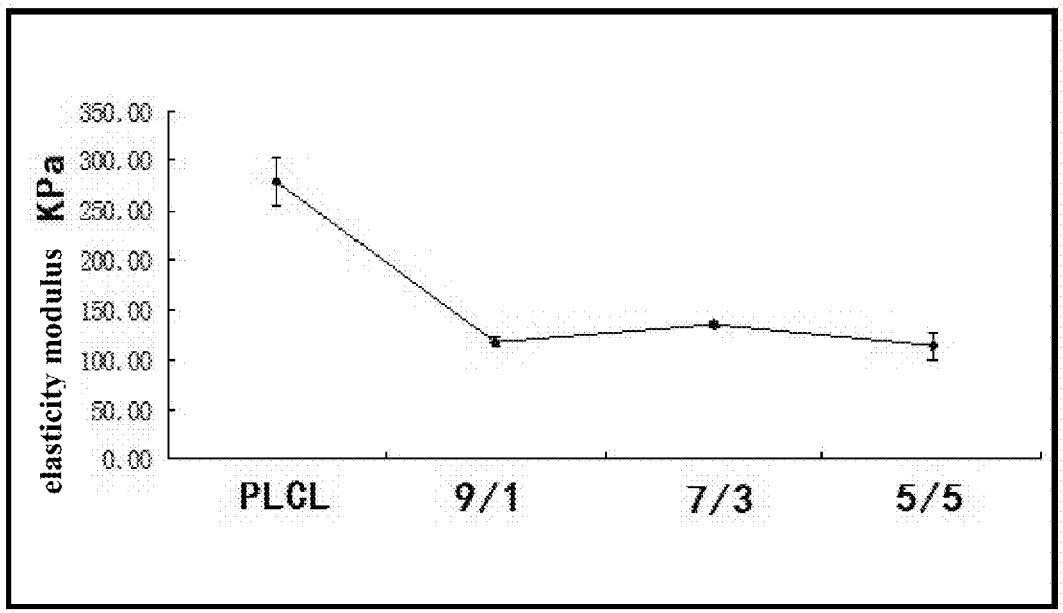
FIG. 1 illustrates an elasticity modulus of a repair material with multi-purpose for an abdominal wall hernia prepared with a mixed solution of a PLCL and an MPEG2000-PLLA6000 copolymer.

Referring to the drawings, PLCL is corresponding to a preferred embodiment 1; 9/1 illustrates a mass ratio between the PLCL and the MPEG-PLLA is 9:1 (which is corresponding to preferred embodiments 1 and 4); 7/3 illustrates the mass ratio between the PLCL and the MPEG-PLLA is 7:3 (which is corresponding to preferred embodiments 2 and 5); 5/5 illustrates the mass ratio between the PLCL and the MPEG-PLLA is 5:5 (which is corresponding to preferred embodiments 3 and 6).

DETAILED DESCRIPTION OF THE PREFERRED EMBODIMENT

Referring to the drawings, a repair material with multi-purpose for an abdominal wall hernia of the present invention is further illustrated, for helping persons skilled in the art to completely, accurately and thoroughly understand inventive ideas and technical schemes of the present invention.

In a field of hernia repair materials, PLCL, MPEG and PLLA have certain meanings. In the field, the PLCL is a lactide/caprolactone copolymer; the MPEG is methoxypolyethylene glycols, and the PLLA is poly L-lactic acid. For example, MPEG2000 illustrates methoxypolyethylene glycols with a molecular weight of 2000, and PLLA6000 illustrates poly L-lactic acid with a molecular weight of 6000; MPEG5000 illustrates methoxypolyethylene glycols with a molecular weight of 5000, and PLLA5000 illustrates poly L-lactic acid with a molecular weight of 5000. In preferred embodiments of the present invention, the PLCL and the MPEG-PLLA copolymer are commercially available. According to the preferred embodiments of the present invention, the PLCL is an L-lactide/caprolactone copolymer, wherein a mole ratio between L-lactide and caprolactone is 50:50, and an intrinsic viscosity thereof at 25° C. is 1.0-1.5 dl/g.

Preferred Embodiment 1

1) Solution Preparation 1-1) material: PLCL, MPEG2000-PLLA6000, acetone.

1-2) equipment: 1000 ml flask, 250 ml cylinder, 250 ml conical flask.

1-3) environment: class 100,000 workshop.

1-4) equipments are processed with dry heat sterilization at 165° C. for 2 h, and are washed with acetone before using.

1-5) preparing 10 g MPEG2000-PLLA6000 and opening after reaching a room temperature, pouring into a 1000 ml flask, and adding acetone; sealing the flask and placing in an environment of 40° C. for dissolving; then adding 90 g PLCL and thoroughly stirring, and adding the acetone for reaching a volume of 1000 mL, wherein a mixed solution obtained is for later use (a mass ratio between the PLCL and the MPEG2000-PLLA6000 is 9:1).

2) Membrane Preparation 2-1) material: the mixed solution.

2-2) equipment: 50 ml cylinder, 100 ml cylinder, tweezers, ePTFE board.

2-3) environment: humidity: <20%; temperature: room temperature.

2-4) moulds and equipments for preparation are cleaned with 75% alcohol and dried in shade.

2-5) placing a mould on worktable, taking the mixed solution with a volume corresponding to the mould, pouring into the mould for leveling, and waiting for obtaining an absorbable membrane material.

3) Clean ultrasonically cleaning with 60% alcohol solution for 15 min, gently swinging, and drying.

Preferred Embodiment 2

1) Solution preparation 1-1) material: PLCL, MPEG2000-PLLA6000, acetone.

1-2) equipment: 1000 ml flask, 250 ml cylinder, 250 ml conical flask.

1-3) environment: class 100,000 workshop.

1-4) equipments are processed with dry heat sterilization at 165° C. for 2 h, and are washed with acetone before using.

1-5) preparing 30 g MPEG2000-PLLA6000 and opening after reaching a room temperature, pouring into a 1000 ml flask, and adding acetone; sealing the flask and placing in an environment of 40° C. for dissolving; then adding 70 g PLCL and thoroughly stirring, and adding the acetone for reaching a volume of 1000 mL, wherein a mixed solution obtained is for later use (a mass ratio between the PLCL and the MPEG2000-PLLA6000 is 7:3).

2) Membrane Preparation 2-1) material: the mixed solution.

2-2) equipment: 50 ml cylinder, 100 ml cylinder, tweezers, ePTFE board.

2-3) environment: humidity: <20%; temperature: room temperature.

2-4) moulds and equipments for preparation are cleaned with 75% alcohol and dried in shade.

2-5) placing a mould on worktable, taking the mixed solution with a volume corresponding to the mould, pouring into the mould for leveling, and waiting for obtaining an absorbable membrane material.

3) Clean ultrasonically cleaning with 60% alcohol solution for 15 min, gently swinging, and drying.

Preferred Embodiment 3

1) Solution Preparation 1-1) material: PLCL, MPEG2000-PLLA6000, acetone.

1-2) equipment: 1000 ml flask, 250 ml cylinder, 250 ml conical flask.

1-3) environment: class 100,000 workshop.

1-4) equipments are processed with dry heat sterilization at 165° C. for 2 h, and are washed with acetone before using.

1-5) preparing 50 g MPEG2000-PLLA6000 and opening after reaching a room temperature, pouring into a 1000 ml flask, and adding acetone; sealing the flask and placing in an environment of 40° C. for dissolving; then adding 50 g PLCL and thoroughly stirring, and adding the acetone for reaching a volume of 1000 mL, wherein a mixed solution obtained is for later use (a mass ratio between the PLCL and the MPEG2000-PLLA6000 is 5:5).

2) Membrane Preparation 2-1) material: the mixed solution.

2-2) equipment: 50 ml cylinder, 100 ml cylinder, tweezers, ePTFE board.

2-3) environment: humidity: <20%; temperature: room temperature.

2-4) moulds and equipments for preparation are cleaned with 75% alcohol and dried in shade.

2-5) placing a mould on worktable, taking the mixed solution with a volume corresponding to the mould, pouring into the mould for leveling, and waiting for obtaining an absorbable membrane material.

3) Clean ultrasonically cleaning with 60% alcohol solution for 15 min, gently swinging, and drying.

Preferred Embodiment 4

1) Solution Preparation 1-1) material: PLCL, MPEG5000-PLLA5000, acetone.

1-2) equipment: 1000 ml flask, 250 ml cylinder, 250 ml conical flask.

1-3) environment: class 100,000 workshop.

1-4) equipments are processed with dry heat sterilization at 165° C. for 2 h, and are washed with acetone before using.

1-5) preparing 10 g MPEG5000-PLLA5000 and opening after reaching a room temperature, pouring into a 1000 ml flask, and adding acetone; sealing the flask and placing in an environment of 40° C. for dissolving; then adding 90 g PLCL and thoroughly stirring, and adding the acetone for reaching a volume of 1000 mL, wherein a mixed solution obtained is for later use (a mass ratio between the PLCL and the MPEG5000-PLLA5000 is 9:1).

2) Membrane Preparation 2-1) material: the mixed solution.

2-2) equipment: 50 ml cylinder, 100 ml cylinder, tweezers, ePTFE board.

2-3) environment: humidity: <20%; temperature: room temperature.

2-4) moulds and equipments for preparation are cleaned with 75% alcohol and dried in shade.

2-5) placing a mould on worktable, taking the mixed solution with a volume corresponding to the mould, pouring into the mould for leveling, and waiting for obtaining an absorbable membrane material.

3) Clean ultrasonically cleaning with 60% alcohol solution for 15 min, gently swinging, and drying.

Preferred Embodiment 5

1) Solution Preparation 1-1) material: PLCL, MPEG5000-PLLA5000, acetone.

1-2) equipment: 1000 ml flask, 250 ml cylinder, 250 ml conical flask.

1-3) environment: class 100,000 workshop.

1-4) equipments are processed with dry heat sterilization at 165° C. for 2 h, and are washed with acetone before using.

1-5) preparing 30 g MPEG5000-PLLA5000 and opening after reaching a room temperature, pouring into a 1000 ml flask, and adding acetone; sealing the flask and placing in an environment of 40° C. for dissolving; then adding 70 g PLCL and thoroughly stirring, and adding the acetone for reaching a volume of 1000 mL, wherein a mixed solution obtained is for later use (a mass ratio between the PLCL and the MPEG5000-PLLA5000 is 3:7).

2) Membrane Preparation 2-1) material: the mixed solution.

2-2) equipment: 50 ml cylinder, 100 ml cylinder, tweezers, ePTFE board.

2-3) environment: humidity: <20%; temperature: room temperature.

2-4) moulds and equipments for preparation are cleaned with 75% alcohol and dried in shade.

2-5) placing a mould on worktable, taking the mixed solution with a volume corresponding to the mould, pouring into the mould for leveling, and waiting for obtaining an absorbable membrane material.

3) Clean ultrasonically cleaning with 60% alcohol solution for 15 min, gently swinging, and drying.

Preferred Embodiment 6

1) Solution Preparation 1-1) material: PLCL, MPEG5000-PLLA5000, acetone.

1-2) equipment: 1000 ml flask, 250 ml cylinder, 250 ml conical flask.

1-3) environment: class 100,000 workshop.

1-4) equipments are processed with dry heat sterilization at 165° C. for 2 h, and are washed with acetone before using.

1-5) preparing 50 g MPEG5000-PLLA5000 and opening after reaching a room temperature, pouring into a 1000 ml flask, and adding acetone; sealing the flask and placing in an environment of 40° C. for dissolving; then adding 50 g PLCL and thoroughly stirring, and adding the acetone for reaching a volume of 1000 mL, wherein a mixed solution obtained is for later use (a mass ratio between the PLCL and the MPEG5000-PLLA5000 is 5:5).

2) Membrane Preparation 2-1) material: the mixed solution.

2-2) equipment: 50 ml cylinder, 100 ml cylinder, tweezers, ePTFE board.

2-3) environment: humidity: <20%; temperature: room temperature.

2-4) moulds and equipments for preparation are cleaned with 75% alcohol and dried in shade.

2-5) placing a mould on worktable, taking the mixed solution with a volume corresponding to the mould, pouring into the mould for leveling, and waiting for obtaining an absorbable membrane material.

3) Clean ultrasonically cleaning with 60% alcohol solution for 15 min, gently swinging, and drying.

Comparison 1

1) Solution Preparation 1-1) material: PLCL, acetone.

1-2) equipment: 1000 ml flask, 250 ml cylinder, 250 ml conical flask.

1-3) environment: class 100,000 workshop.

1-4) equipments are processed with dry heat sterilization at 165° C. for 2 h, and are washed with acetone before using.

1-5) preparing 100 g PLCL and opening after reaching a room temperature, pouring into a 1000 ml flask, and adding acetone; sealing the flask and placing in an environment of 40° C. for dissolving; then adding the acetone for reaching a volume of 1000 mL, wherein a mixed solution obtained is for later use.

2) Membrane Preparation 2-1) material: the PLCL solution.

2-2) equipment: 50 ml cylinder, 100 ml cylinder, tweezers, ePTFE board.

2-3) environment: humidity: <20%; temperature: room temperature.

2-4) moulds and equipments for preparation are cleaned with 75% alcohol and dried in shade.

2-5) placing a mould on worktable, taking the mixed solution with a volume corresponding to the mould, pouring into the mould for leveling, and waiting for obtaining an absorbable membrane material.

3) Clean ultrasonically cleaning with 60% alcohol solution for 15 min, gently swinging, and drying.

Figure 2:
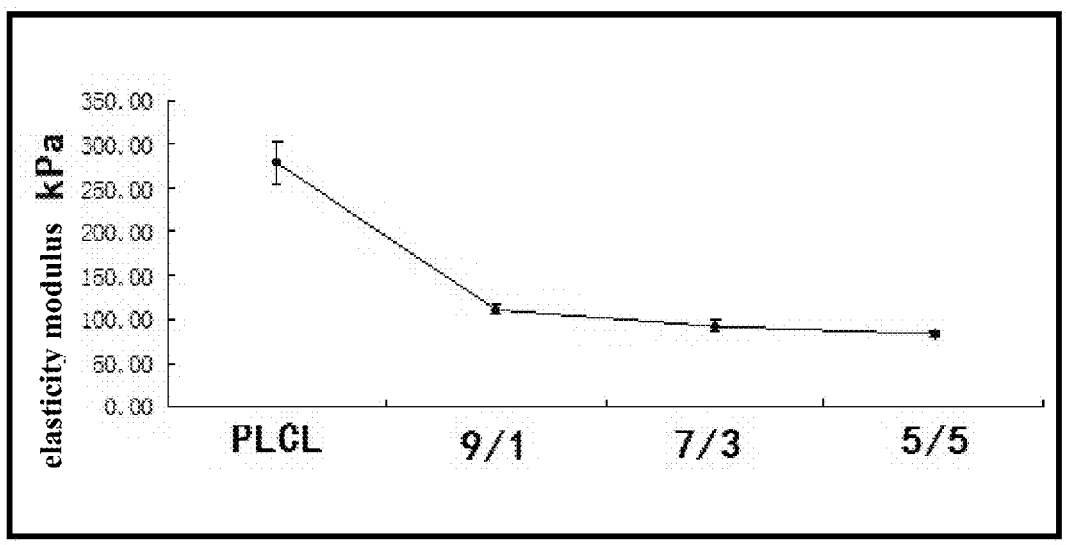
FIG. 2 illustrates an elasticity modulus of a repair material with multi-purpose for an abdominal wall hernia prepared with a mixed solution of a PLCL and an MPEG5000-PLLA5000 copolymer.
Figure 3:
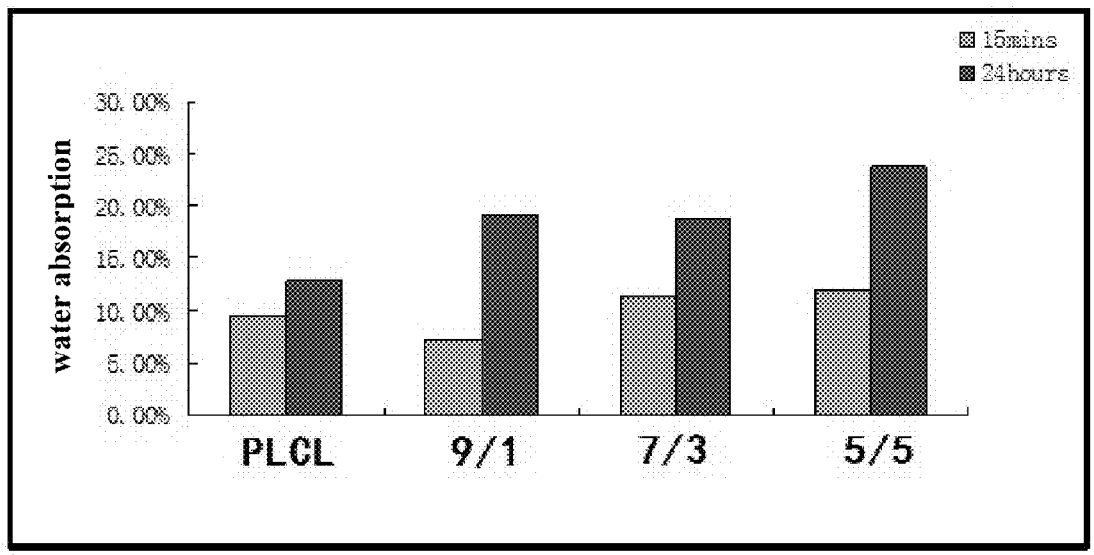
FIG. 3 illustrates a water absorption of the repair material prepared with the mixed solution of the PLCL and the MPEG2000-PLLA6000 copolymer.
Figure 4:
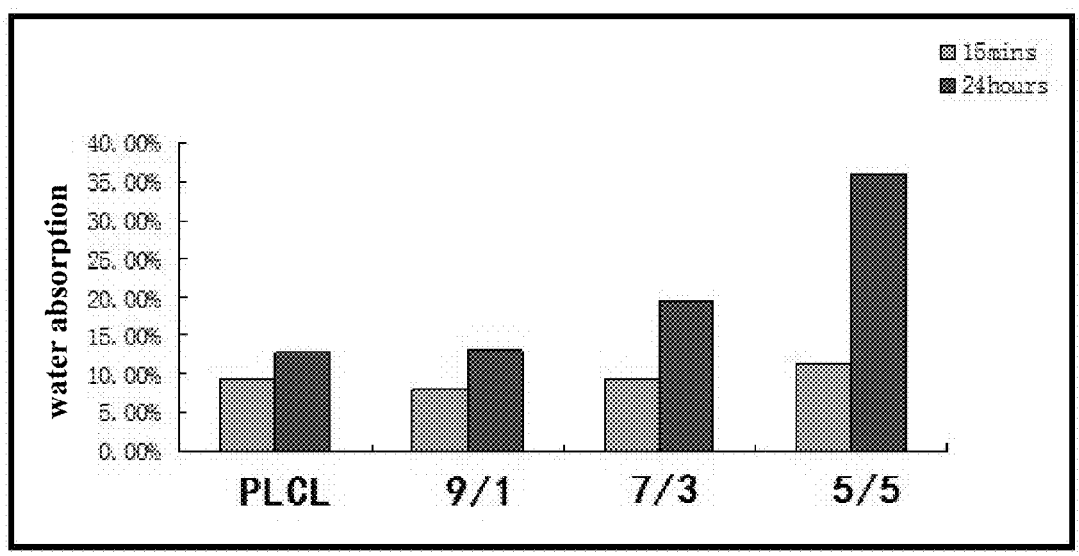
FIG. 4 illustrates a water absorption of the repair material prepared with the mixed solution of the PLCL and the MPEG5000-PLLA5000 copolymer.
Figure 5:
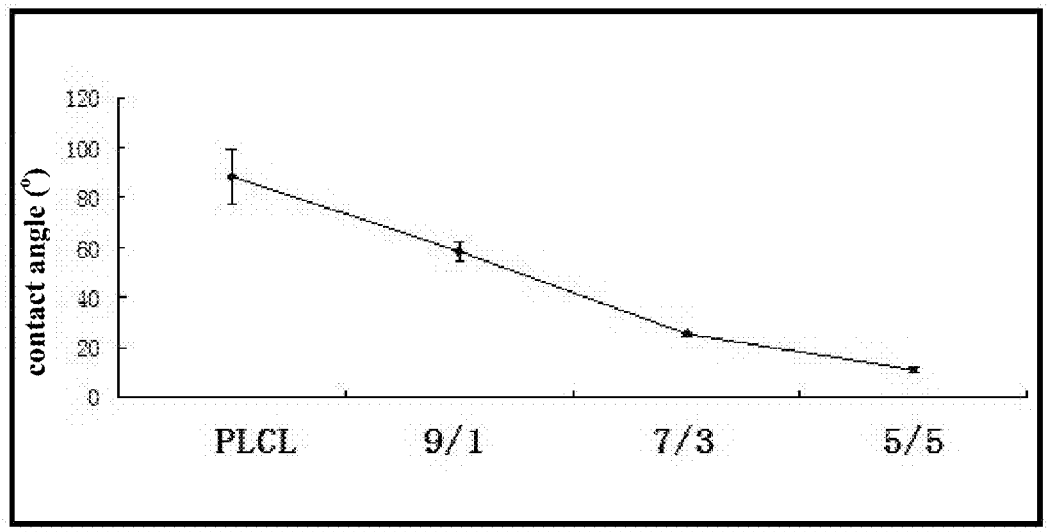
FIG. 5 illustrates a contact angle of the repair material prepared with the mixed solution of the PLCL and the MPEG2000-PLLA6000 copolymer.
Figure 6:
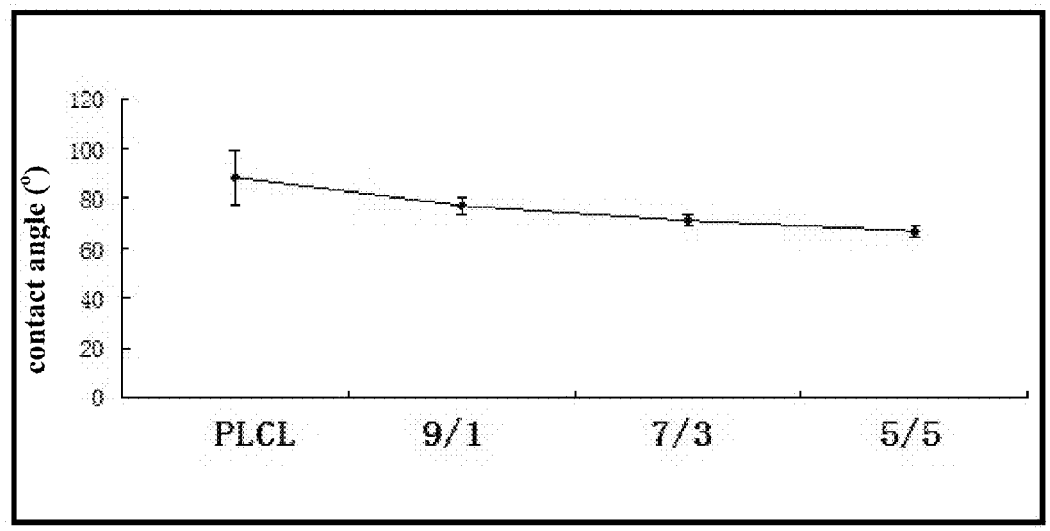
FIG. 6 illustrates a contact angle of the repair material prepared with the mixed solution of the PLCL and the MPEG5000-PLLA5000 copolymer.
Figure 7:
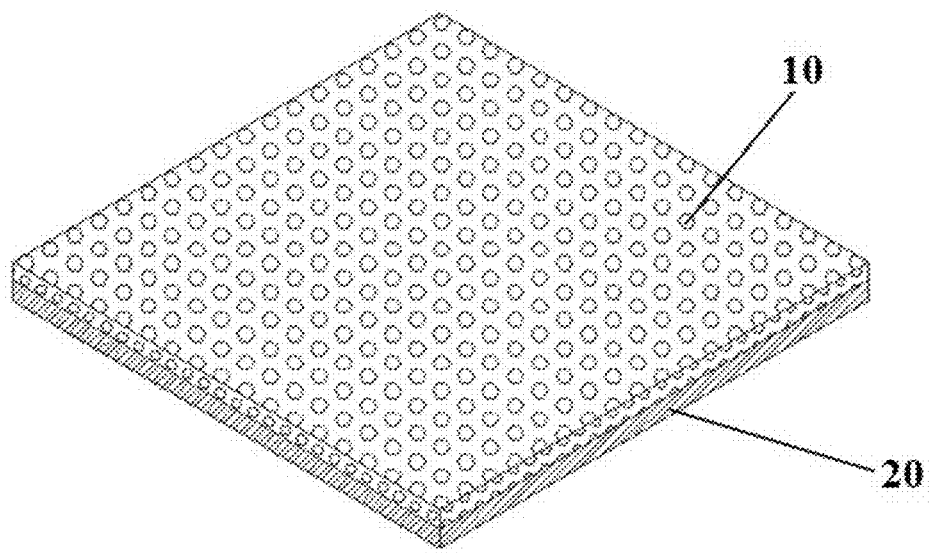
FIG. 7 is a sketch view of an anti-adhesion patch with an internal drainage function.
Figure 8:
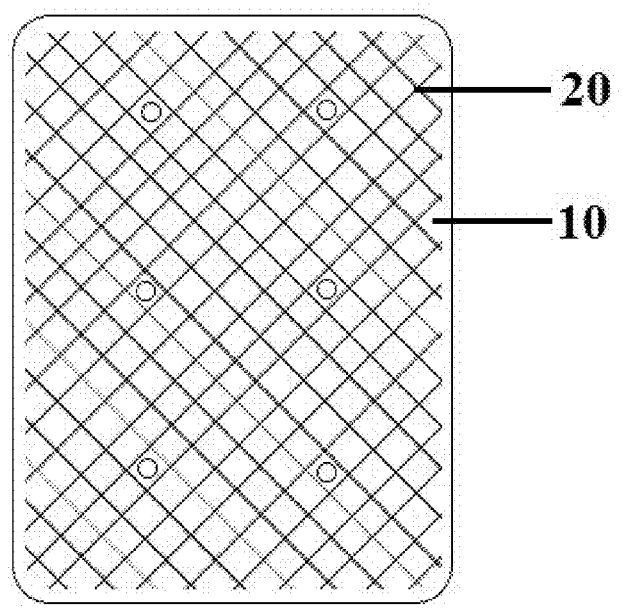
FIG. 8 is a sketch view of a composite patch having an anti-adhesion soft membrane.
Figure 9:
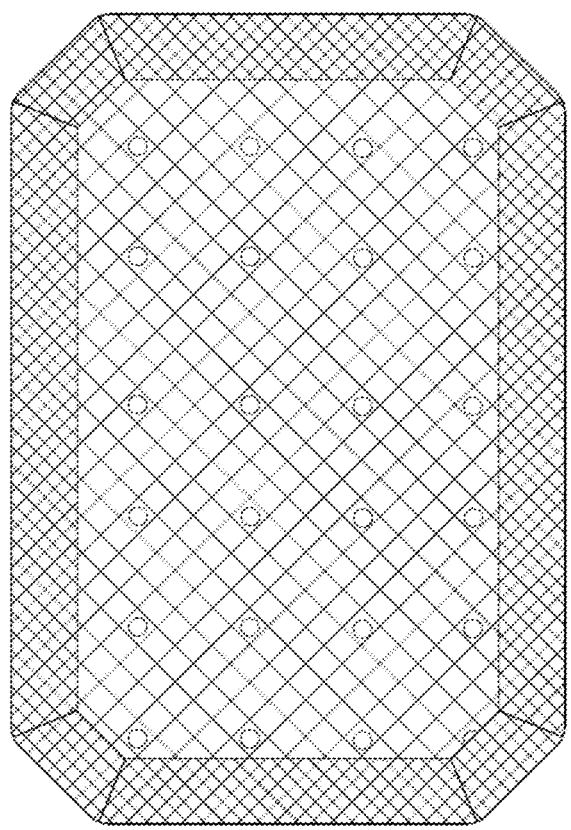
FIG. 9 is a sketch view of an abdominal wall hernia repair mesh designed for open surgeries.

The absorbable membranes (i.e. the repair material with multi-purpose for an abdominal wall hernia) obtained in the preferred embodiments 1-6 and the comparison 1 are performance-tested for respectively obtaining elasticity modulus, water absorption and contact angles thereof, wherein 4 parallel samples are tested for taking an average value. The contact angle refers to an angle between a horizontal line of a solid-liquid interface and a tangent line of a gas-liquid interface at an intersection of three phases. The contact angle is measured with a surface tension instrument, wherein an approach angle is defined as the contact angle, and a working temperature is 25° C. Measured results are illustrated in FIGS. 1-6, wherein it can be concluded that compared with the PLCL, the repair material of the present invention lowers a material rigidity, increases water absorption, as well as reduces the contact angle. As a result, postoperative abdominal wall compliance is sufficient, which basically provides no discomfort, leading to improvement of comfort. Specifically, the contact angle of the repair material, which is obtained by mixing the MPEG2000-PLLA5000 and the PLCL with equal volumes, is less than 20°. However, by mixing PEG-PCL or PEG-PLLA with PLCL, not only the water absorption is less improved, but also the contact angle is maintained at 85°-105°, which is much higher than that of the present invention.

Preferred Embodiment 7

1) Solution Preparation 1-1) material: PLCL, MPEG5000-PLLA5000, acetone.

1-2) equipment: 1000 ml flask, 250 ml cylinder, 250 ml conical flask.

1-3) environment: class 100,000 workshop.

1-4) equipments are processed with dry heat sterilization at 165° C. for 2 h, and are washed with acetone before using.

1-5) preparing 10 g MPEG2000-PLLA6000 and opening after reaching a room temperature, pouring into a 1000 ml flask, and adding acetone; sealing the flask and placing in an environment of 40° C. for dissolving; then adding 90 g PLCL and thoroughly stirring, and adding the acetone for reaching a volume of 1000 mL, wherein a mixed solution obtained is for later use (a mass ratio between the PLCL and the MPEG2000-PLLA6000 is 9:1).

1-6) taking 100 ml mixed solution and adding into a 250 ml conical flask, then adding 100 ml acetone; and sealing the conical flask and thoroughly shaking, wherein a coating mixed solution obtained is for later use.

2) Fusion 2-1) material: the mixed solution, the coating mixed solution, polypropylene mesh.

2-2) equipment: 50 ml cylinder, 100 ml cylinder, tweezers, ePTFE board.

2-3) environment: humidity: <20%; temperature: room temperature.

2-4) moulds and equipments for preparation are cleaned with 75% alcohol and dried in shade.

2-5) placing a polypropylene mesh in the coating mixed solution for once, naturally drying, then placing in a middle of the ePTFE board for being flattened, and waiting for further use.

2-6) placing a mould on worktable, taking the mixed solution with a volume corresponding to the mould, pouring into the mould for leveling, and waiting for 6 h.

2-7) tiling the mesh on a PLCL membrane, adjusting for completely press-fitting, setting a temperature at 80° C. and heating for 30 min.

3) Punching 3-1) equipment: knife, punching device.

3-2) environment: class 100,000 workshop.

3-3) cutting off the absorbable membrane at edges.

3-4) punching on a composite patch with the punching device (¢1), which is started from one corner of the mesh, wherein punching once every 3 mesh grids in both horizontal and vertical directions for ensuring even distribution of holes punched.

4) Clean ultrasonically cleaning with 60% alcohol solution for 15 min, gently swinging, and drying.

5) Package 6) vacuum-dry 7) sterilization sterilizing by a γ ray with 15-25 KGy.

Preferred embodiment 8: the methods in preferred embodiments 1-7 are also adaptable for preparing hernia repair patches with functions as follows:

1) A method for preparing an anti-adhesion patch with an internal drainage function, comprising steps of:

(1) immersing a polypropylene mesh in a poly lactide-caprolactone coating solution, and drying for obtaining a poly lactide-caprolactone coated polypropylene mesh;

(2) pouring the poly lactide-caprolactone coating solution into a mould, statically evaporating for obtaining a poly lactide-caprolacton membrane;

(3) press-fitting the poly lactide-caprolactone coated polypropylene mesh obtained in the step (1) to the poly lactide-caprolacton membrane and statically evaporating;

(4) punching drainage holes on an absorbable membrane; and (5) pouring colored absorbable membrane coating solution into a mould, statically evaporation for obtaining a marked membrane; trimming the marked membrane, and fitting onto the absorbable membrane.

2) A method for preparing a composite patch having an anti-adhesion soft membrane, comprising steps of:

(1) immersing a polypropylene mesh in an absorbable layer coating solution, and drying for obtaining an absorbable layer coated polypropylene mesh;

(2) pouring the absorbable coating solution into a mould, statically evaporating for obtaining an absorbable membrane;

(3) press-fitting the absorbable layer coated polypropylene mesh obtained in the step (1) to the absorbable membrane and statically evaporating;

(4) punching drainage holes on the absorbable membrane; and (5) pouring colored absorbable membrane coating solution into a mould, statically evaporation for obtaining a marked membrane; trimming the marked membrane, and fitting onto the absorbable membrane.

3) A method for preparing an abdominal wall hernia repair mesh designed for open surgeries, comprising steps of:

(1) immersing a polypropylene mesh in an absorbable layer coating solution, and drying for obtaining an absorbable layer coated polypropylene mesh;

(2) pouring the absorbable coating solution into a mould, statically evaporating for obtaining an absorbable membrane; and (3) press-fitting the absorbable layer coated polypropylene mesh obtained in the step (1) to the absorbable membrane and statically evaporating;

One skilled in the art will understand that the embodiment of the present invention as shown in the drawings and described above is exemplary only and not intended to be limiting.

It will thus be seen that the objects of the present invention have been fully and effectively accomplished. Its embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A repair material with multi-purpose for an abdominal wall hernia, comprising: an absorbable membrane, wherein the absorbable membrane is prepared with a mixed solution of a PLCL (L-lactide/caprolactone copolymer) and an MPEG-PLLA (Methoxy (polyethylene glycol)-b-poly(L-lactide)) copolymer;

wherein in the L-lactide/caprolactone copolymer, a mole ratio between L-lactide and caprolactone is from 50:50 to 90:10; and an intrinsic viscosity of the L-lactide/caprolactone copolymer at 25° C. is 1.0-2.5 dl/g;

wherein in the MPEG-PLLA copolymer, a molecular weight of MPEG is 2000-10000, and a molecular weight of PLLA is 3000-8000.

2. The repair material, as recited in claim 1, wherein the molecular weight of the MPEG is 2000-5000, and the molecular weight of the PLLA is 5000-6000.

3. The repair material, as recited in claim 1, wherein the repair material comprises a polypropylene mesh with an absorbable coating thereon, and the absorbable membrane press-fitted on the polypropylene mesh; the absorbable coating is formed by applying the mixed solution of the PLCL and the MPEG-PLLA copolymer to the polypropylene mesh.

4. The repair material, as recited in claim 1, wherein a mole ratio between the PLCL and the MPEG-PLLA copolymer in the mixed solution is from 5:5 to 7:3.

5. The repair material, as recited in claim 3, wherein a mole ratio between the PLCL and the MPEG-PLLA copolymer in the mixed solution is from 5:5 to 7:3.

6. The repair material, as recited in claim 3, wherein a density of the polypropylene mesh is 20-80 g/m$^2$, a thickness thereof is 1-5 mm; and a single hole area of the polypropylene mesh is 3-20 mm$^2$.

7. The repair material, as recited in claim 1, wherein the absorbable membrane has a drainage hole thereon.

8. The repair material, as recited in claim 3, wherein the absorbable membrane has a drainage hole thereon.

* * * * *